(12) United States Patent
Craig et al.

(10) Patent No.: US 8,153,442 B2
(45) Date of Patent: Apr. 10, 2012

(54) STABILIZATION OF SIGNAL GENERATION IN PARTICLES USED IN ASSAYS

(75) Inventors: Alan R. Craig, Wilmington, DE (US); Zhu Teng, Boothwyn, PA (US); Carsten Schelp, Hockessin, DE (US); Jason Snyder, Newark, DE (US); Christine Moran, Elkton, MD (US)

(73) Assignee: Siemens Healthcare Diagnostics Inc., Deerfield, IL (US)

( * ) Notice: Subject to any disclaimer, the term of this patent is extended or adjusted under 35 U.S.C. 154(b) by 280 days.

(21) Appl. No.: 12/603,364

(22) Filed: Oct. 21, 2009

(65) Prior Publication Data

US 2011/0091978 A1 Apr. 21, 2011

(51) Int. Cl.
*G01N 1/00* (2006.01)
*G01N 21/76* (2006.01)
*G01N 33/546* (2006.01)

(52) U.S. Cl. ............... 436/176; 436/8; 436/73; 436/82; 436/84; 436/164; 436/166; 436/172; 436/501; 436/518; 436/534; 422/52; 435/7.8; 435/968

(58) Field of Classification Search .............. 436/8, 73, 436/82, 84, 164, 166, 172, 174, 805, 501, 436/518, 524, 531, 534; 422/52, 82.05, 82.08; 435/7.1, 7.8, 968
See application file for complete search history.

(56) References Cited

U.S. PATENT DOCUMENTS

| | | | |
|---|---|---|---|
| 4,259,313 A | 3/1981 | Frank et al. | |
| 4,283,382 A | 8/1981 | Frank et al. | |
| 4,719,182 A | 1/1988 | Burdick et al. | |
| 4,735,907 A | 4/1988 | Schaeffer et al. | |
| 4,784,912 A | 11/1988 | Schaeffer et al. | |
| 4,876,190 A | 10/1989 | Recktenwald | |
| 5,043,265 A | 8/1991 | Tanke et al. | |
| 5,316,909 A | 5/1994 | Xu | |
| 5,457,184 A * | 10/1995 | Lehn et al. ................. | 534/15 |
| 5,578,498 A | 11/1996 | Singh et al. | |
| 5,618,732 A | 4/1997 | Pease et al. | |
| 5,627,074 A * | 5/1997 | Mathis et al. ............... | 436/518 |
| 5,637,509 A * | 6/1997 | Hemmila et al. ............ | 436/537 |
| 5,672,478 A | 9/1997 | Singh et al. | |
| 5,709,994 A | 1/1998 | Pease et al. | |
| 5,811,311 A | 9/1998 | Singh et al. | |
| 5,876,935 A | 3/1999 | Pankratz et al. | |
| 5,936,070 A | 8/1999 | Singh et al. | |
| 6,180,354 B1 | 1/2001 | Singh et al. | |
| 6,187,594 B1 | 2/2001 | Kraus et al. | |
| 6,197,594 B1 | 3/2001 | Weindel et al. | |
| 6,319,670 B1 | 11/2001 | Sigal et al. | |
| 6,340,599 B1 | 1/2002 | Singh et al. | |
| 6,406,667 B1 | 6/2002 | Singh et al. | |
| 6,406,913 B1 * | 6/2002 | Ullman et al. ............... | 435/41 |
| 6,482,653 B1 | 11/2002 | Kraus et al. | |
| 6,632,599 B1 | 10/2003 | Kraus et al. | |
| 6,692,975 B2 | 2/2004 | Singh et al. | |
| 6,750,032 B2 | 6/2004 | Kraus et al. | |
| 6,797,481 B1 | 9/2004 | Ullman et al. | |
| 6,881,536 B1 | 4/2005 | Shah et al. | |
| 6,916,667 B2 | 7/2005 | Singh et al. | |
| 7,033,775 B2 | 4/2006 | Ullman et al. | |
| 7,101,682 B2 | 9/2006 | Ullman et al. | |
| 2003/0180780 A1 | 9/2003 | Feng et al. | |
| 2004/0121490 A1 | 6/2004 | Singh et al. | |
| 2005/0118727 A1 | 6/2005 | Schelp et al. | |
| 2005/0170529 A1 | 8/2005 | Murthy et al. | |
| 2005/0214875 A1 | 9/2005 | Singh et al. | |
| 2006/0166376 A1 | 7/2006 | Craig et al. | |
| 2006/0223193 A1 | 10/2006 | Song et al. | |
| 2006/0246597 A1 | 11/2006 | Feaster et al. | |
| 2006/0246601 A1 | 11/2006 | Song et al. | |
| 2006/0270063 A1 | 11/2006 | Craig et al. | |
| 2007/0020700 A1 | 1/2007 | Carpenter et al. | |
| 2007/0048807 A1 | 3/2007 | Song | |
| 2007/0082346 A1 | 4/2007 | Schelp et al. | |
| 2010/0233725 A1 * | 9/2010 | Singh et al. ................. | 435/7.1 |

OTHER PUBLICATIONS

Li et al. "A Chemiluminescent Metalloimmunoassay Based on Silver Deposition on Colloidal Gold Labels." Analytical Biochemistry [online], Dec. 15, 2006 [Retrieved on Dec. 6, 2010], vol. 359, Iss. 2 pp. 247-252, Retrieved from the Internet; <URL:http://www.sciencedirect.com>.

* cited by examiner

*Primary Examiner* — Maureen Wallenhorst
(74) *Attorney, Agent, or Firm* — Theodore J. Leitereg

(57) ABSTRACT

Methods and reagents are disclosed for conducting assays. Embodiments of the present methods and reagents are concerned with a solid support such as, for example, a particle. The support includes a chemiluminescent composition that includes a metal chelate. The present inventors observed that, when such support such as, e.g., particles, were employed in assays for the determination of an analyte, stability of signal output by the chemiluminescent composition associated with the particle was unacceptably reduced as compared to particles including other chemiluminescent compositions. In accordance with embodiments of the present invention, the stability of signal output from such particles is enhanced by including in a medium that contains the particles a sufficient amount of one or more stabilizing agents, which may be a chelating agent and/or a metal chelate such as, for example, the metal chelate that is associated with the particle.

21 Claims, No Drawings

STABILIZATION OF SIGNAL GENERATION IN PARTICLES USED IN ASSAYS

BACKGROUND

This invention relates to particles, which are capable of generating signal, for use in methods, compositions and kits for determining an analyte in a sample. The invention further relates to the stabilization of signal generated by such particles.

The clinical diagnostic field has seen a broad expansion in recent years, both as to the variety of materials of interest that may be readily and accurately determined, as well as the methods for the determination. Most methods involve generation of a signal in relation to the presence and/or amount of one or more analytes in a sample. Luminescent compounds, such as fluorescent compounds and chemiluminescent compounds, find wide application in the assay field because of their ability to emit light. Particles, such as latex particles, liposomes and the like have been utilized in assays. Dyed latex particles have been used previously not only in immunoassays but also for other diverse uses such as photodynamic therapy and as pigments. Both absorptive dyes and dyes that impart fluorescent or chemiluminescent properties have been incorporated into particles. In one particular approach, particles that comprise one or more metal chelates such as, for example, lanthanide chelates, are employed for generating a signal.

An induced luminescence immunoassay is described in U.S. Pat. Nos. 5,340,716 and 6,251,581, which disclosures are incorporated herein by reference. In one approach the assay uses a particle incorporating a photosensitizer and a label particle incorporating a chemiluminescent compound. The label particle is conjugated to a specific binding pair (sbp) member that is capable of binding to an analyte to form a complex, or to a second sbp member to form a complex, in relation to the presence of the analyte. If the analyte is present, the photosensitizer and the chemiluminescent compound come into close proximity. The photosensitizer generates singlet oxygen and activates the chemiluminescent compound when the two labels are in close proximity. The activated chemiluminescent compound subsequently produces light. The amount of light produced is related to the amount of the complex formed, which in turn is related to the amount of analyte present. In one particular approach, the chemiluminescent particles comprise one or more metal chelates such as, for example, lanthanide chelates.

In a variation of the induced luminescence method, a particulate support is employed that comprises both (a) a photosensitizer capable upon irradiation of generating singlet oxygen and (b) a chemiluminescent compound capable of being activated by singlet oxygen. The methods allow for generating delayed luminescence, which can be realized upon irradiation of the support. The methods have application to the determination of an analyte in a medium suspected of containing the analyte. One method comprises subjecting a medium suspected of containing an analyte to conditions under which a complex of sbp members is formed in relation to the presence of the analyte and determining whether the sbp member complex has formed by employing as a label a particulate composition having both chemiluminescent and photosensitizer properties. Upon activation of the photosensitizer property singlet oxygen is generated and activates the chemiluminescent property. Such compositions and methods are described in U.S. Pat. No. 5,709,994, the relevant disclosure of which is incorporated herein by reference.

There is a continuing need to maximize signal generation in label reagents for use in assays. Signal response to changes in the concentration of analyte is an important consideration in assay development. Such label reagents should provide for maximized performance including sensitivity.

SUMMARY

One embodiment of the present invention is a method of enhancing the stability of a chemiluminescent reagent, which comprises a solid support having associated therewith a chemiluminescent composition comprising a complex of a metal and one or more chelating agents. The chemiluminescent reagent is present in a medium. The method comprises incorporating into the medium one or more stabilizing agents, which may be a chelating agent and/or a metal chelate such as, for example, the complex itself, in an amount sufficient to enhance the stability of the chemiluminescent reagent of the solid support.

Another embodiment of the present invention is a chemiluminescent reagent for determining the presence and/or amount of an analyte in a sample suspected of containing the analyte. The chemiluminescent reagent is present in a medium. The chemiluminescent reagent comprises a solid support having associated therewith a member of a specific binding pair and having incorporated therein a complex of a metal and one or more chelating agents. The medium further comprises one or more stabilizing agents, which may be a chelating agent and/or a metal chelate such as, for example, the complex itself, where the amount of the one or more stabilizing agents in the medium is sufficient to enhance the stability of the chemiluminescent reagent of the solid support.

Another embodiment of the present invention is a method for determining the presence and/or amount of an analyte in a sample suspected of containing the analyte. A combination is provided in a medium. The combination comprises (i) the sample, (ii) the above-mentioned chemiluminescent reagent, and (iii) a photosensitizer associated with a particle and being capable of generating singlet oxygen. A specific binding pair member for the analyte is associated with at least one of the solid support or the particle. The combination is subjected to conditions for binding of the analyte to the specific binding pair member for the analyte. The photosensitizer is irradiated with light and the amount of luminescence generated by the chemiluminescent composition is determined. The amount of luminescence is related to the amount of the analyte in the sample.

DETAILED DESCRIPTION OF SPECIFIC EMBODIMENTS

General Discussion

Embodiments of the present methods and reagents are concerned with a solid support such as, for example, a particle. The support comprises a chemiluminescent composition that comprises a metal chelate. The present inventors observed that, when such support such as, e.g., particles, were employed in assays for the determination of an analyte, stability of signal output by the chemiluminescent composition associated with the particle was unacceptably reduced as compared to particles comprising other chemiluminescent compositions. In accordance with embodiments of the present invention, the stability of signal output from such particles is enhanced by including in a medium comprising the particles a sufficient amount of one or more stabilizing agents, which may be a chelating agent and/or a metal chelate such as, for example, the metal chelate that is associated with the particle.

Performance of a particular assay format at the low end of the medical decision range can be monitored by monitoring the difference in the amount of signal obtained for calibrators spanning the suspected concentration range of interest of the analyte. A large difference or separation between the signal for calibrators such as, for example, calibrator L1 and calibrator L2 or calibrator L2 and calibrator L3, is desired. For example, six calibrators may be employed, arbitrarily named L1-L6. Signal to noise ratio may be evaluated by determining an amount of signal using a calibrator that contains no analyte, arbitrarily designated calibrator L1 (background), and the amount of signal obtained for a calibrator containing a first known amount of analyte above zero, arbitrarily designated calibrator L2. This evaluation may also include determining an amount of signal using calibrator L1 and the amount of signal for a calibrator containing a second known amount of analyte above zero, arbitrarily designated L3. Such an evaluation may also include such determination using calibrators L4, L5, L6 and so forth. The embodiments discussed herein provide for better performance in an assay for an analyte compared to reagents not in accordance with the present embodiments.

A large difference between the signal for calibrators, e.g., calibrator L1 and calibrator L2, or calibrator L1 and calibrator L6, is desired. For good sensitivity in the medical decision range, the difference in the signal detected between calibrator L1 and calibrator L2 is at least about 50%, at least about 75%, at least about 90%, at least about 100%, at least about 125%, at least about 150%, at least about 175%, at least about 200%, at least about 225%, at least about 250%, at least about 275%, at least about 300%, at least about 325%, at least about 350%, at least about 375%, at least about 400%, at least about 425%, and so forth. In some embodiments the signal detected for calibrator L6 is at least about 10 times, at least about 20 times, at least about 30 times, at least about 40 times, at least about 50 times, at least about 60 times, at least about 70 times, at least about 80 times, at least about 90 times, at least about 100 times, greater than the signal detected for calibrator L1. Depending on the assay format, the difference in signal may be an increase in signal or a decrease in signal. Typically, the results of the assays using the calibrators are presented in a graph format wherein the amount of signal is plotted against the concentration of the calibrators. In accordance with embodiments of the present invention the slope of the line between calibrator L1 and calibrator L2 generally is steeper compared with results obtained with assay reagents not in accordance with the present embodiments. Furthermore, the slope of the line from calibrator L1 to calibrator L6 is usually steeper compared with results obtained with assay reagents not in accordance with the present embodiments.

As mentioned above, embodiments of the present invention relate to enhancing the stability of a chemiluminescent reagent, which comprises a solid support having associated therewith a chemiluminescent composition comprising a complex of a metal and one or more chelating agents. The solid support may be comprised of an organic or inorganic, solid or fluid, water insoluble material, which may be transparent or partially transparent. The solid support can have any of a number of shapes, such as particulate, including beads and particles, film, membrane, tube, well, strip, rod, planar surfaces such as, e.g., plate, and the like. Depending on the type of assay, the solid support may or may not be suspendable in the medium in which it is employed. Examples of a suspendable solid support include polymeric materials such as latex particles, lipid bilayers or liposomes, oil droplets, cells and hydrogels, magnetic particles, and the like. Other solid support compositions include polymers, such as nitrocellulose, cellulose acetate, poly (vinyl chloride), polyacrylamide, polyacrylate, polyethylene, polypropylene, poly(4-methylbutene), polystyrene, polymethacrylate, poly (ethylene terephthalate), nylon, poly(vinyl butyrate), etc.; either used by themselves or in conjunction with other materials.

In some embodiments the solid support is a particle. The particles generally have an average diameter of at least about 0.02 microns and not more than about 100 microns. In some embodiments, the particles have an average diameter from about 0.05 microns to about 20 microns or from about 0.3 microns to about 10 microns. The particle may be organic or inorganic, swellable or non-swellable, porous or non-porous, preferably of a density approximating water, generally from about 0.7 g/mL to about 1.5 g/mL, and composed of material that can be transparent, partially transparent, or opaque. The particles can be biological materials such as cells and microorganisms, e.g., erythrocytes, leukocytes, lymphocytes, hybridomas, *streptococcus, Staphylococcus aureus, E. coli*, viruses, and the like. The particles can also be particles comprised of organic and inorganic polymers, liposomes, latex particles, magnetic or non-magnetic particles, phospholipid vesicles, chylomicrons, lipoproteins, and the like. In some embodiments, the particles are chrome particles or latex particles.

A latex particle is a particulate water suspendable water insoluble polymeric material. The latex particle may have particle dimensions of about 20 nm to about 20 mm, or about 100 to about 1000 nm, in diameter. In some embodiments the latex is a substituted polyethylene such as polystyrene-butadiene, polyacrylamide polystyrene, polystyrene with amino groups, poly-acrylic acid, polymethacrylic acid, acrylonitrile-butadiene, styrene copolymers, polyvinyl acetate-acrylate, polyvinyl pyridine, vinyl-chloride acrylate copolymers, and the like. Non-crosslinked polymers of styrene and carboxylated styrene or styrene functionalized with other active groups such as amino, hydroxyl, halo and the like are employed in some embodiments. Copolymers of substituted styrenes with dienes such as butadiene may also be used.

The polymer particles can be formed from addition or condensation polymers. The particles will be readily dispersible in an aqueous medium and can be adsorptive or functionalizable so as to permit conjugation, either directly or indirectly through a linking group, to a member of a signal producing system (sps), a member of a specific binding pair (sbp), and the like. The particles can also be derived from naturally occurring materials, naturally occurring materials that are synthetically modified, and synthetic materials. Among organic polymers of particular interest are polysaccharides, particularly cross-linked polysaccharides, such a agarose, which is available as Sepharose, dextran, available as Sephadex and Sephacryl, cellulose, starch, and the like; addition polymers, such as polystyrene, polyvinyl alcohol, homopolymers and copolymers of derivatives of acrylate and methacrylate, particularly esters and amides having free hydroxyl functionalities, and the like.

The chemiluminescent composition comprises a complex of a metal and one or more chelating agents. Examples of metals that form part of the complex include, for example, rare earth metals, metals in Group VIII, and the like. The rare earth metals comprise the lanthanoids (lanthanide metals) (the 15 elements from lanthanum to lutetium, atomic numbers 57-71). The rare earth metals of particular interest include europium, terbium, dysprosium and samarium. The metals of Group VIII of particular interest include osmium and ruthenium. Rare earth metals will usually have an oxidation state of plus three, ruthenium will have an oxidation state of plus two and osmium will have an oxidation state of plus two. In certain embodiments the metal is selected from the group consisting of europium, terbium, dysprosium, samarium, osmium and ruthenium. In some embodiments the metal is at least hexacoordinated; however, the metal may be octacoordinated or more highly coordinated depending on the metal chelating agent.

The metal chelating agent is a compound in which two or more atoms of the same molecule can coordinate with a metal to form a metal chelate. The two or more atoms may be, for example, oxygen, nitrogen, sulfur, phosphorus and the like. The atoms may be in the form of one or more functionalities such as, for example, ketone, aldehyde, hydroxy, amine, thioketone, thioaldehyde, thiol, and the like. The functionalities may be part of a benzyl group or a condensed aromatic ring system derived from, for example, naphthalene, anthracene, phenanthrene, acridine, pyrene and so forth.

One of the aforementioned metals is coordinated with one or more chelating agents, particle examples of which include, for example, 2-(1',1',1',2',2',3',3'-heptafluoro-4',6'-hexanedion-6'-yl)-naphthylene (NHA), 4,4'-bis(2'',3'',3''-heptafluororo-4'',6''-hexanedion-6''-yl)-o-terphenyl (BHHT), phenanthroline (phen) and phenanthroline-related compounds (derivatives of phenanthroline) such as, e.g., phenanthroline carboxylic acid, 4,7-diphenyl-1,10-phenanthroline (DPP), and the like, 3-(2-thienoyl, 1,1,1-trifluoroacetone (TTA), 3-(2-naphthoyl)-1,1,1-trifluoroacetone (NPPTA), (trioctyl phosphine oxide (TOPO), triphenyl phosphine oxide (TPPO). 3-benzoyl-1,1,1-trifluoroacetone (BFTA), 2,2-dimethyl-4-perfluorobutyoyl-3-butanone (fod), 2,2'-dipyridyl (bpy), salicylic acid, bipyridylcarboxylic acid, aza crown ethers trioctylphosphine oxide, aza cryptands, and so forth as well as combinations of the above. As mentioned above, in some embodiments the metal in the metal chelate is at least hexacoordinated. The metal chelate will be uncharged; thus, the number of acidic groups provided by the chelating agent will equal the oxidation state of the metal. Usually, the metal chelating agent is relatively hydrophobic so as to impart solubility of the metal chelate in non-polar solvents. Exemplary of particular metal chelates, by way of illustration and not limitation, include $Eu(TTA)_3DPP$, $Eu(NTA)_3DPP$, $Eu(NHA)_3DPP$, $Eu(BHHT)_2DPP$, metal chelates as discussed in U.S. Pat. No. 6,916,667 (for example, columns 5-9) and U.S. Patent Application No. 20060270063 (column 3-4), the relevant disclosures of which are incorporated herein by reference, and so forth.

Many of the chelating agents and metal chelates are known in the art and many are commercially available. In general, metal chelates can be prepared from a metal chelating agent by combining a metal chloride with the desired ratio of molecules of metal chelating agent in an organic solvent such as, e.g., acetonitrile, and sufficient base, e.g., pyridine, to take up hydrochloric acid that is produced during the reaction. For example, metal chelates can be prepared by a procedure such as that described by Shinha, A. P., "Fluorescences and laser action in rare earth chelates," Spectroscopy Inorganic Chemistry, Vol 2, (1971), 255-288.

The manner of association of the metal chelate with the solid support depends on the nature of the support, the nature of the metal chelate, the nature of the solvent, and so forth. The association may be by adsorption of the metal chelate by the support, covalent bonding of the metal chelate to the support, dissolution or dispersion of the metal chelate in the solid support, non-covalent bonding of the metal chelate to the support by means of binding pair members (e.g., avidin-biotin, digoxin-antibody for digoxin, etc.), for example. In this manner the metal chelate may be "associated with" the solid support.

The association of the metal chelate with latex particles may involve incorporation during formation of the particles by polymerization, incorporation into preformed particles, usually by noncovalent dissolution into the particles, and the like. In some approaches a solution of the metal chelate is employed. Solvents that may be utilized include alcohols, including ethanol, ethoxyethanol, ethylene glycol and benzyl alcohol; amides such as dimethyl formamide, formamide, acetamide and tetramethyl urea and the like; sulfoxides such as dimethyl sulfoxide and sulfolane; and ethers such as carbitol, ethyl carbitol, dimethoxy ethane and the like, and water. The use of solvents having high boiling points in which the particles are insoluble permits the use of elevated temperatures to facilitate dissolution of the compounds into the particles and are particularly suitable. The solvents may be used singly or in combination. A solvent should be selected for the reaction that does not interfere with the luminescence of the metal chelates because of their intrinsic properties or ability to be removed from the particles. In some embodiments aromatic solvents may be employed such as, for example, dibutylphthalate, benzonitrile, naphthonitrile, dioctylterephthalate, dichlorobenzene, diphenylether, dimethoxybenzene, and the like.

Generally, the temperature employed during the procedure will be chosen to maximize the quantum yield of the metal chelate particles with the proviso that the particles should not melt or become aggregated at the selected temperature. Elevated temperatures are normally employed. The temperatures for the procedure will generally range from about 20° C. to about 200° C., or about 50° C. to about 170° C. It has been observed that some compounds that are nearly insoluble at room temperature are soluble in, for example, low molecular weight alcohols, such as ethanol and ethylene glycol and the like, at elevated temperatures. Carboxylated modified latex particles have been shown to tolerate low molecular weight alcohols at such temperatures.

In some embodiments the chemiluminescent reagents are employed in assays for the determining the presence and/or amount of an analyte in a sample suspected of containing the analyte. In such embodiments a binding partner for the analyte is associated with the solid support. The manner of association of the metal chelate with the solid support depends on the nature of the support, the nature of the binding partner for the analyte, and so forth. The association may be by adsorption of the binding partner by the support, covalent bonding of the binding partner to the support, non-covalent bonding of the binding partner to the support by means of binding pair members (e.g., avidin-biotin, digoxin-antibody for digoxin, etc.), for example. In this manner the binding partner for the analyte may be "associated with" the solid support. Methods for associating the binding partner for the analyte with the solid support are well-known in the art and will not be repeated here.

In some embodiments a surface of the solid support comprises one or more coatings wherein the coating may be, for example, an amino-derivatized polysaccharide, a carboxylmethyl polysaccharide, a dextran aldehyde (dexal). The functionalized coating may be employed for reaction with a protein such as, for example, an antibody, to form a product thereby covalently binding the protein to the solid support. For example, aminodextran or carboxymethyldextran can be utilized for forming conjugates to specific binding pair members. Coupling the dextran to a protein, for example, can then be carried out through formation of an amide.

In some embodiments a surface of the solid support does not comprise a coating (i.e., the surface is free of a coating material such as those mentioned above). In these embodiments, a binding partner for an analyte is associated with the solid support utilizing a functionality on the surface of the solid support such as, for example, a carboxyl, an amine, a hydroxyl, and so forth. In a particular embodiment, carboxylated latex beads may be employed. Some of the present embodiments have particular application to supports such as particles having associated therewith a chemiluminescent composition where the surface of the support is substantially free from a coating.

After preparation of the chemiluminescent reagent, i.e., the solid support having associated with it a metal chelate, the chemiluminescent reagent is placed in a suitable medium for storage until used in an assay. In many embodiments the medium is an aqueous medium, usually an aqueous buffered medium. The aqueous medium may be solely water or may include from 0.1 to about 40 volume percent of a cosolvent such as, for example, an organic solvent, which may be an alcohol, ether, ester, amine, amide, and the like. The pH for the medium will usually be in the range of about 4 to about 11, or in the range of about 5 to about 10, or in the range of about 6.5 to about 9.5. The pH will usually be based upon the nature of the solid support, the nature of the metal chelate, the nature of the metal chelating agents, and so forth. Various buffers may be used to achieve the desired pH and maintain the pH. Illustrative buffers include borate, phosphate, carbonate, tris, barbital, PIPES, HEPES, MES, ACES, MOPS, BICINE, and the like. The particular buffer employed is not critical, but with a particular chemiluminescent reagent one or another buffer may be preferred. In some embodiments, the medium in which the chemiluminescent reagent is stored is substantially similar to, or the same as, the medium for an assay for an analyte where the chemiluminescent reagent is one of the assay reagents employed.

The method in accordance with embodiments of the present invention comprises incorporating into the storage medium for the chemiluminescent reagent one or more stabilizing agents, which may be a chelating agent and/or a metal chelate, in an amount sufficient to enhance the stability of the chemiluminescent reagent in the solid support. In many embodiments the stabilizing agent or agents are selected from the same chelating agent of agents that form part of the metal chelate associated with the solid support of the chemiluminescent reagent or from chelating agents that are structurally similar to the chelating agent in the metal chelate. Structural similarity may result from the spatial arrangement of the atoms of the chelating agent, from derivatization of the chelating agent of the metal chelate such as, for example, to impart greater solubility of the chelating agent in the medium in which the chemiluminescent reagent is stored, and so forth.

A group or functionality that imparts hydrophilicity or water solubility is a hydrophilic functionality, which increases wettability of solids with water and the solubility in water of compounds to which it is bound. Such functional group or functionality can be a substituent having 1 to 50 or more atoms and can include a sulfonate, sulfate, phosphate, amidine, phosphonate, carboxylate, hydroxyl particularly polyols, amine, ether, amide, and the like. Illustrative functional groups are carboxyalkyl, sulfonoxyalkyl, $CONHOCH_2COOH$, $CO$-(glucosamine), sugars, dextran, cyclodextrin, $SO_2NHCH_2COOH$, $SO_3H$, $CONHCH_2CH_2SO_3H$, $PO_3H_2$, $OPO_3H_2$, hydroxyl, carboxyl, ketone, and combinations thereof. Such a group or functionality may be introduced into the chelating agent by methods that are well-known in the art for introducing such groups or functionalities into compounds.

In instances where a stabilizing chelating agent other than the chelating agent of the chemiluminescent reagent is employed, such stabilizing agent may be selected from the group of metal chelating agents set forth above. As a general rule, the chelating ability of a stabilizing agent other than that of the metal chelate should be at least as strong as, or stronger, than the chelating ability of the chelating agent of the metal chelate. In many embodiments where the stabilizing agent comprises a metal chelate, the metal chelate is the same as the metal chelate associated with the solid support of the chemiluminescent reagent. However, in some instances a stabilizing metal chelate agent other than the metal chelate of the chemiluminescent reagent may be employed. Such metal chelate for use as a stabilizing agent may be selected from the group of metal chelate set forth above.

In a specific embodiment of the above, by way of illustration and not limitation, the chemiluminescent reagent is a latex particle having incorporated therein $Eu(NHA)_3DPP$ as the metal chelate. The stabilizing agent may be the chelating agent NHA or DPP or a combination of both NHA and DPP or the stabilizing agent may be $Eu(NHA)_3DPP$ itself. The stabilizing agent is incorporated into the medium in which the chemiluminescent reagent is stored. As may be appreciated, in the above example the chelating agent employed as the stabilizing agent may be any of the aforementioned metal chelating agents.

The stabilizing agent is employed, in the medium in which the chemiluminescent reagent is stored, in an amount sufficient to enhance the stability of the chemiluminescent reagent of the solid support. The amount of the stabilizing agent is dependent on the nature of the support, the nature of the metal chelate, the nature and properties of the stabilizing agent, and so forth. The stabilizing agent should exhibit reasonable solubility in the medium in which the chemiluminescent reagent is stored. In many instances, this medium is an aqueous medium and, thus, the stabilizing agent should be soluble in water or water-cosolvent combinations to the extent of at least about 50%, or at least about 55%, or at least about 60%, or at least about 65%, or at least about 70%, or at least about 75%, or at least about 80%, or at least about 85%, or at least about 90%, or at least about 95%, or at least about 99%, for example. The amount of the stabilizing agent in the medium that is sufficient to stabilize the chemiluminescent reagent and enhance it signal output may be obtained empirically by conducting assays with the chemiluminescent reagent stored in differing concentrations of the stabilizing and selecting the concentration that provides the desired level of signal output and results in a desired level of stability. In many embodiments the amount of stabilizing agent in the medium is about 0.001% to about 10%, or about 0.01% to about 5%, or about 0.02% to about 2%, or about 0.001% to about 5%, or about 0.01% to about 2%, or about 0.02% to about 1%, or about 0.005% to about 10%, or about 0.01% to about 3%, or about 0.02% to about 3%, for example, wherein percent is weight to volume.

The stabilizing agent employed may be a derivative of a metal chelating agent of the metal chelate wherein a functionality that enhances the water solubility of the chelating agent is introduced into the chelating agent to impart greater solubility in an aqueous medium without interfering to any substantial degree with the chelating properties of the chelating agent. In addition or as an alternative, the amount of any cosolvent such as an organic solvent in the medium may be adjusted to attain the desired level of solubility of the stabilizing agent.

It is interesting to note that the use of the stabilizing agent in the medium in which the chemiluminescent reagent is stored to enhance the stability of the reagent is unexpected. Incorporation of a stabilizing agent into the support of the chemiluminescent reagent did not provide enhanced stability or enhanced signal output.

General Description of Assays for an Analyte Utilizing the Present Reagents

The present invention has application to any assay that utilizes a support having associated with the support a metal chelate. The reagents of the present embodiments may be used in most assays for the determination of an analyte that is an sbp member. In general, in such assays the reagents comprise, among others, a receptor for the analyte. A sample suspected of containing an analyte is combined in an assay medium with a receptor for the analyte. The binding of the receptor to the analyte, if present, is detected. A chemiluminescent reagent in accordance with the above embodiments is employed as a label reagent in the detection of this binding event wherein the receptor is a binding partner for the analyte of interest. The assay can be performed either without separation (homogeneous) or with separation (heterogeneous) of any of the assay components or products.

Heterogeneous assays usually involve one or more separation steps and can be competitive or non-competitive. A variety of competitive and non-competitive heterogeneous assay formats are disclosed in Davalian, et al., U.S. Pat. No. 5,089,390, column 14, line 25 to column 15, line 9, incorporated herein by reference. In a typical competitive heterogeneous assay, a support having an antibody for analyte bound thereto is contacted with a medium containing the sample and analyte analog conjugated to a detectable label such as an enzyme. Analyte in the sample competes with the analyte analog for binding to the antibody. After separating the support and the medium, the label activity of the support or the medium is determined by conventional techniques and is related to the amount of analyte in the sample.

An "analyte analog" is a modified drug that can compete with the analogous analyte for a receptor, the modification providing means to join an analyte analog to another molecule. The analyte analog will usually differ from the analyte by more than replacement of a hydrogen with a bond which links the drug analog to a hub or label, but need not. The analyte analog binds to the receptor in a manner similar to the binding of analyte to the receptor. The analyte analog may be, for example, the analyte conjugated to another molecule through a linking group, an antibody directed against the idiotype of an antibody to the analyte, and so forth.

One general group of immunoassays that may be employed includes immunoassays using a limited concentration of antibody. Another group of immunoassays involves the use of an excess of one or more of the principal reagents such as, for example, an excess of an antibody for the analyte. Another group of immunoassays are separation-free homogeneous assays in which the labeled reagents modulate the label signal upon analyte-antibody binding reactions. Another group of assays includes labeled antibody reagent limited competitive assays for analyte that avoid the use of problematic labeled haptens. In this type of assay, the solid phase immobilized analyte is present in a constant, limited amount. The partition of a label between the immobilized analyte and free analyte depends on the concentration of analyte in the sample.

Some assays utilize a signal producing system (sps) that employs a chemiluminescent reagent such as a metal chelate associated with a support and has at least first and second sps members. The designation "first" and "second" is completely arbitrary and is not meant to suggest any order or ranking among the sps members or any order of addition of the sps members in the present methods. The sps members may be related in that activation of one member of the sps produces a product such as, e.g., light, which results in activation of another member of the sps. In some embodiments of known assays, the sps members comprise a sensitizer and a chemiluminescent composition where activation of the sensitizer results in a product that activates the chemiluminescent composition. The second sps member usually generates a detectable signal that relates to the amount of bound and/or unbound sps member, i.e. the amount of sps member bound or not bound to the analyte being detected or to an agent that reflects the amount of the analyte to be detected. In accordance with embodiments of the present invention, the chemiluminescent composition is the chemiluminescent reagent described above wherein the chemiluminescent reagent is stored in a medium that contains a stabilizing amount of a stabilizing agent.

In some embodiments the first sps member is a sensitizer, such as, for example, a photosensitizer and the second sps member is a chemiluminescent composition that is activated as a result of the activation of the first sps member. The sensitizer may be any moiety that upon activation produces a product that activates the chemiluminescent composition, which in turn generates a detectable signal. In many embodiments the sensitizer is capable of generating singlet oxygen upon activation.

In some embodiments the sensitizer is a photosensitizer for generation of singlet oxygen usually by excitation with light. The photosensitizer can be photoactivatable (e.g., dyes and aromatic compounds) or chemi-activated (e.g., enzymes and metal salts). When excited by light the photosensitizer is usually a compound comprised of covalently bonded atoms, usually with multiple conjugated double or triple bonds. The compound should absorb light in the wavelength range of about 200 to about 1100 nm, or about 300 to about 1000 nm, or about 450 to about 950 nm, with an extinction coefficient at its absorbance maximum greater than about 500 $M^{-1}$ $cm^{-1}$, or at least about 5000 $M^{-1}$ $cm^{-1}$, or at least about 50,000 $M^{-1}$ $cm^{-1}$ at the excitation wavelength. Photosensitizers that are to be excited by light will be relatively photostable and will not react efficiently with singlet oxygen. Several structural features are present in most useful photosensitizers. Most photosensitizers have at least one and frequently three or more conjugated double or triple bonds held in a rigid, frequently aromatic structure. They will frequently contain at least one group that accelerates intersystem crossing such as a carbonyl or imine group or a heavy atom selected from rows 3-6 of the periodic table, especially iodine or bromine, or they may have extended aromatic structures. Typical photosensitizers include acetone, benzophenone, 9-thioxanthone, eosin, 9,10-dibromoanthracene, methylene blue, metallo-porphyrins, such as hematoporphyrin, phthalocyanines, chlorophylis, rose bengal, buckminsterfullerene, etc., and derivatives of these compounds having substituents of 1 to 50 atoms for rendering such compounds more lipophilic or more hydrophilic and/or as attaching groups for attachment, for example, to an sps member or an sbp member.

The photosensitizers useful in the above methods include other substances and compositions that can produce singlet oxygen with or, less preferably, without activation by an external light source. Thus, for example, molybdate salts and chloroperoxidase and myeloperoxidase plus bromide or chloride ion (Kanofsky, J. Biol. Chem. (1983) 259 5596) have been shown to catalyze the conversion of hydrogen peroxide to singlet oxygen and water. Also included within the scope of photosensitizers are compounds that are not true sensitizers but which on excitation by heat, light, or chemical activation will release a molecule of singlet oxygen. The best known members of this class of compounds includes the endoperoxides such as 1,4-biscarboxyethyl-1,4-naphthalene endoperoxide, 9,10-diphenylanthracene-9,10-endoperoxide and 5,6,11,12-tetraphenyl naphthalene 5,12-endoperoxide. Heating or direct absorption of light by these compounds releases singlet oxygen. Examples of other photosensitizers that may be utilized are those set forth in U.S. Pat. Nos. 5,340,716 and 6,251,581, the relevant disclosures of which are incorporated herein by reference.

The present invention has application in the induced luminescence immunoassay referred to in U.S. Pat. No. 5,340,716 (Ullman) entitled "Assay Method Utilizing Photoactivated Chemiluminescent Label" ("induced luminescence assay"), which disclosure is incorporated herein by reference. In one approach the assay uses a particle incorporating a photosensitizer and a label particle incorporating a chemiluminescent compound. The label particle is conjugated to an sbp member that is capable of binding to an analyte to form a complex, or to a second sbp member to form a complex, in relation to the presence of the analyte. If the analyte is present, the photosensitizer and the chemiluminescent compound come into close proximity. The photosensitizer generates singlet oxygen and activates the chemiluminescent compound when the two labels are in close proximity. The activated chemiluminescent compound subsequently produces light. The amount of light produced is related to the amount of the complex formed, which in turn is related to the amount of analyte present. In accordance with embodiments of the present invention, the chemiluminescent compound is the chemiluminescent reagent described above wherein the chemiluminescent reagent is stored in a medium that contains a stabilizing amount of a stabilizing agent.

In some embodiments of the induced luminescence assay, a particle is employed, which comprises the chemiluminescent compound associated therewith such as by incorporation therein or attachment thereto. The particles are conjugated to avidin. An sbp member that binds to the analyte, i.e., a binding partner for the analyte, is bound to biotin. Incubation of the above reagents yields a single reagent wherein the sbp member is bound to the particle in an irreversible manner. Biotin may then be added in an amount sufficient to react with any remaining unoccupied avidin binding sites. A second sbp member that binds to the analyte, i.e., a second binding partner for the analyte, is part of a biotin-receptor conjugate. Avidin is conjugated to a second set of particles having a photosensitizer associated therewith. Incubation of these reagents results in a single reagent having the second sbp member bound to the photosensitizer particles in an irreversible manner. The reaction medium is incubated to allow the particles to bind to the analyte by virtue of the binding of the sbp members to the analyte. Then, the medium is irradiated with light to excite the photosensitizer, which is capable in its excited state of activating oxygen to a singlet state. Because the chemiluminescent compound of one of the sets of particles is now in close proximity to the photosensitizer by virtue of the presence of the analyte, it is activated by the singlet oxygen and emits luminescence. The medium is then examined for the presence and/or the amount of luminescence or light emitted, the presence thereof being related to the presence of the analyte. In accordance with embodiments of the present invention, the chemiluminescent reagent of the present embodiments wherein the chemiluminescent reagent is stored in a medium that contains a stabilizing amount of a stabilizing agent is employed as the particle reagent with chemiluminescent compound associated therewith.

The phrase "at least" as used herein means that the number of specified items may be equal to or greater than the number recited. The phrase "about" as used herein means that the number recited may differ by plus or minus 10%; for example, "about 5" means a range of 4.5 to 5.5.

The sample to be analyzed is one that is suspected of containing analyte. The samples are preferably from humans or animals and include biological fluids such as whole blood, serum, plasma, sputum, lymphatic fluid, semen, vaginal mucus, feces, urine, spinal fluid, saliva, stool, cerebral spinal fluid, tears, mucus, and the like; biological tissue such as hair, skin, sections or excised tissues from organs or other body parts; and so forth. In many instances, the sample is whole blood, plasma or serum and, in a particular embodiment the sample is whole blood.

The sample can be prepared in any convenient medium. Conveniently, the sample may be prepared in an assay medium, which is discussed more fully below. In some instances a pretreatment may be applied to the sample such as, for example, to lyse blood cells, and the like. Such pretreatment is usually performed in a medium that does not interfere subsequently with an assay. An aqueous medium is preferred for the pretreatment.

As discussed briefly above, the assays are normally carried out in an aqueous buffered medium at a moderate pH, generally that which provides optimum assay sensitivity. The aqueous medium may be solely water or may include from 0.1 to about 40 volume percent of a cosolvent. The pH for the medium will usually be in the range of about 4 to about 11, more usually in the range of about 5 to about 10, and preferably in the range of about 6.5 to about 9.5. The pH will usually be a compromise between optimum binding of the binding members of any specific binding pairs, the pH optimum for other reagents of the assay such as members of the signal producing system, and so forth. Various buffers may be used to achieve the desired pH and maintain the pH during the determination. Illustrative buffers include borate, phosphate, carbonate, tris, barbital, PIPES, HEPES, MES, ACES, MOPS, BICINE, and the like. The particular buffer employed is not critical, but in an individual assay one or another buffer may be preferred.

Various ancillary materials may be employed in the above methods. For example, in addition to buffers the medium may comprise stabilizers for the medium and for the reagents employed. Frequently, in addition to these additives, proteins may be included, such as albumins; organic solvents such as formamide; quaternary ammonium salts; polyanions such as dextran sulfate; binding enhancers, e.g., polyalkylene glycols; or the like. The medium may also comprise agents for preventing the formation of blood clots. Such agents are well known in the art and include, for example, EDTA, EGTA, citrate, heparin, and the like. The medium may also comprise one or more preservatives as are known in the art such as, for example, sodium azide, neomycin sulfate, PROCLIN® 300, Streptomycin, and the like. All of the above materials are present in a concentration or amount sufficient to achieve the desired effect or function.

One or more incubation periods may be applied to the medium at one or more intervals including any intervals between additions of various reagents mentioned above. The medium is usually incubated at a temperature and for a time sufficient for binding of various components of the reagents to occur. Moderate temperatures are normally employed for carrying out the method and usually constant temperature, preferably, room temperature, during the period of the measurement. Incubation temperatures normally range from about 5° C. to about 99° C., usually from about 15° C. to about 70° C., more usually 20° C. to about 45° C. The time period for the incubation is about 0.2 seconds to about 24 hours, or about 1 second to about 6 hours, or about 2 seconds to about 1 hour, or about 1 to about 15 minutes. The time period depends on the temperature of the medium and the rate of binding of the various reagents, which is determined by the association rate constant, the concentration, the binding constant and dissociation rate constant. Temperatures during measurements will generally range from about 10° C. to about 50° C., or from about 15° C. to about 40° C.

The concentration of the analyte that may be assayed generally varies from about $10^{-5}$ to about $10^{-17}$M, more usually from about $10^{-6}$ to about $10^{-14}$ M. Considerations, such as whether the assay is qualitative, semi-quantitative or quantitative (relative to the amount of the analyte present in the sample), the particular detection technique and the concentration of the analyte normally determine the concentrations of the various reagents.

The concentrations of the various reagents in the assay medium will generally be determined by the concentration range of interest of the analyte, the nature of the assay, and the like. However, the final concentration of each of the reagents is normally determined empirically to optimize the sensitivity of the assay over the range. That is, a variation in concentration of analyte that is of significance should provide an accurately measurable signal difference. Considerations such as the nature of the signal producing system and the nature of the analytes normally determine the concentrations of the various reagents.

As mentioned above, the sample and reagents are provided in combination in the medium. While the order of addition to the medium may be varied, there will be certain preferences for some embodiments of the assay formats described herein. The simplest order of addition, of course, is to add all the materials simultaneously and determine the effect that the assay medium has on the signal as in a homogeneous assay. Alternatively, each of the reagents, or groups of reagents, can be combined sequentially. Optionally, an incubation step may be involved subsequent to each addition as discussed above.

Examination Step

In a next step of the methods in accordance with the present disclosure, the medium is examined for the presence of a complex comprising the analyte and the antibody for the analyte. The presence and/or amount of the complex indicate the presence and/or amount of the analyte in the sample.

The phrase "measuring the amount of an analyte" refers to the quantitative, semiquantitative and qualitative determination of the analyte. Methods that are quantitative, semiquantitative and qualitative, as well as all other methods for determining the analyte, are considered to be methods of measuring the amount of the analyte. For example, a method, which merely detects the presence or absence of the analyte in a sample suspected of containing the analyte, is considered to be included within the scope of the present invention. The terms "detecting" and "determining," as well as other common synonyms for measuring, are contemplated within the scope of the present invention.

In many embodiments the examination of the medium involves detection of a signal from the medium where the signal produced results from the involvement of the chemiluminescent reagent in accordance with the present embodiments. The presence and/or amount of the signal are related to the presence and/or amount of the analyte in the sample. The particular mode of detection depends on the nature of the sps.

As discussed above, there are numerous methods by which a label of an sps can produce a signal detectable by external means. Activation of a signal producing system depends on the nature of the signal producing system members. For an sps member that is a sensitizer that is activated by light, the sps member is irradiated with light. Other activation methods will be suggested to those skilled in the art in view of the disclosures herein.

When a photosensitizer is used, the photosensitizer serves to activate the chemiluminescent reagent, in particular, the metal chelate, when the medium containing the above reactants is irradiated. The medium is irradiated with light having a wavelength of sufficient energy to convert the photosensitizer to an excited state and render it capable of activating molecular oxygen to singlet oxygen. When bound to an sbp member, the photosensitizer concentration may be very low, frequently about $10^{-6}$ to about $10^{-12}$ M or lower. Generally, for the above embodiments involving a photosensitizer, the medium is irradiated with light having a wavelength of about 300 to about 1200 nm, or about 450 to about 950, or about 550 to about 800 nm.

The period of irradiation will depend on the lifetime of the activated chemiluminescent reagent, the light intensity and the desired emission intensity. For short-lived activated chemiluminescent reagents, the period may be less than a second, usually about a millisecond but may be as short as a microsecond where an intense flashlamp or laser is used. For longer-lived activated chemiluminescent reagents, the irradiation period can be longer and a less intense steady light source can be used. In general, the integrated light intensity over the period of irradiation should be sufficient to excite at least 0.1% of the photosensitizer molecules, preferably at least 30%, and, most preferably, every photosensitizer molecule will be excited at least once.

A helium-neon laser is an inexpensive light source for excitation at 632.6 nm. Photosensitizers that absorb light at this wavelength are compatible with the emission line of a helium-neon laser and are, therefore, particularly useful in the present methods in which photosensitizers are employed. Other light sources include, for example, other lasers such as Argon, YAG, He/Cd, and ruby; photodiodes; mercury, sodium and xenon vapor lamps; incandescent lamps such as tungsten and tungsten/halogen; and flashlamps.

Temperatures during measurements generally range from about 10° C. to about 70° C., or from about 20° C. to about 45° C., or about 20° C. to about 25° C. In one approach standard curves are formed using known concentrations of the analytes to be screened. As discussed above, calibrators and other controls may also be used.

The luminescence or light produced in any of the above approaches can be measured visually, photographically, actinometrically, spectrophotometrically or by any other convenient means to determine the amount thereof, which is related to the amount of analyte in the medium. The examination for presence and/or amount of the signal also includes the detection of the signal, which is generally merely a step in which the signal is read. The signal is normally read using an instrument, the nature of which depends on the nature of the signal. The instrument may be a spectrophotometer, fluorometer, absorption spectrometer, luminometer, chemiluminometer, and the like. The presence and amount of signal detected is related to the presence and amount of the analyte present in a sample.

Kits Comprising Reagents for Conducting Assays

The present chemiluminescent compositions stored in a medium, which comprises a stabilizing agent in accordance with the present embodiments, and other reagents for conducting a particular assay may be present in a kit useful for conveniently performing an assay for the determination of an analyte. In some embodiments a kit comprises in packaged combination a biotin-antibody for analyte conjugate, streptavidin-sensitizer particles and analyte analog-chemiluminescent particles as well as any other reagents for performing the assay, the nature of which depend upon the particular assay format. In some embodiments a kit comprises antibody for analyte bound to chemiluminescent particles, streptavidin-sensitizer particles and a biotin-antibody for analyte conjugate as well as any other reagents for performing the assay, the nature of which depend upon the particular assay format. The chemiluminescent particles can comprise a metal chelate as the chemiluminescent compound.

The reagents may each be in separate containers or various reagents can be combined in one or more containers depending on the cross-reactivity and stability of the reagents. The kit can further include other separately packaged reagents for conducting an assay such as additional sbp members, ancillary reagents, and so forth.

The relative amounts of the various reagents in the kits can be varied widely to provide for concentrations of the reagents that substantially optimize the reactions that need to occur during the present method and further to optimize substantially the sensitivity of the assay. Under appropriate circumstances one or more of the reagents in the kit can be provided as a dry powder, usually lyophilized, including excipients, which on dissolution will provide for a reagent solution having the appropriate concentrations for performing a method or assay in accordance with the present invention. The kit can further include a written description of a method in accordance with the present invention as described above.

The following examples further describe the specific embodiments of the invention by way of illustration and not limitation and are intended to describe and not to limit the scope of the invention. Parts and percentages disclosed herein are by weight to volume unless otherwise indicated.

EXAMPLES

Unless indicated otherwise, reagents were from Sigma-Aldrich (Milwaukee, Wis.). Testing was carried out using a prototype of the DIMENSION® ExL analyzer, available from Siemens Healthcare Diagnostics Inc., Newark Del. The instrument was employed using induced luminescence immunoassay technology and was equipped with an appropriate reader. Stability studies were conducted using the cardiac troponin I (cTnI) assay (Siemens Healthcare Diagnostics Inc., Part No. RF 623) with changes as set forth below.

Example 1

Preparation of stabilizing solution: 12 mg of 2-(1',1',1',2',2',3',3'-heptafluoro-4',6'-hexanedion-6'-yl)-naphthalene (NHA) was dissolved into 1.2 ml 99% ethanol. A 0.2 ml aliquot and a 1.0 ml aliquot of the above solution were each added to separate 1-liter portions of LOCI® diluent HEPES buffer pH 7.2 (Item No. 781000.308 from Siemens Healthcare Diagnostics Inc.). These two bottles of solution were shaken at 4° C. for 3 days and then filtered separately through a 0.45 micron filter while cold. The resulting NHA concentration in each LOCI diluent buffer solution was 0.02% and 0.1%, respectively. As a result, three different LOCI diluents were available for carrying out the stabilities studies below. The three diluents were LOCI diluent containing 0 mg/mL (Control), 2 mg/mL (Diluent 1) and 10 mg/mL (Diluent 2) of NHA, respectively, as a stabilizing agent. These three diluents were employed to prepare the chemiluminescent reagents of the commercial cTnI assay.

Principles of the procedure of the commercial cTnI assay: The TNI method is a homogeneous, sandwich chemiluminescent immunoassay based on LOCI® technology. The LOCI® reagents include two synthetic bead reagents and a biotinylated anti-cardiac troponin monoclonal antibody fragment. The first bead reagent (Sensibeads) is coated with streptavidin and contains photosensitizer dye. The second bead reagent (Chemibeads) is coated with a second anti-cardiac troponin I monoclonal antibody and contains chemiluminescent dye. Sample is incubated with Chemibeads and biotinylated antibody to form bead-cardiac troponin I-biotinylated antibody sandwiches. Sensibeads are added and bind to the biotin to form bead-pair immunocomplexes. Illumination of the complex at 680 nm generates singlet oxygen from Sensibeads which diffuses into the Chemibeads, triggering a chemiluminescent reaction. The resulting signal is measured at 612 nm and is a direct function of the cardiac troponin I concentration in the sample.

Reagents. The assay reagents were as follows (Table 1) wherein the wells are wells of the FLEX® cartridge of the commercial cTnI assay:

TABLE 1

| Wells | Form | Ingredient | Concentration | Source |
| --- | --- | --- | --- | --- |
| 1-2 | Liquid | Biotinylated Antibody | 8 µg/mL | Mouse monoclonal |
| 3-4 | Liquid | Troponin I Chemibeads | 190 µg/mL | Mouse monoclonal |
| 5-6 | Liquid | Streptavidin Sensibead | 1500 µg/mL | Recombinant E. coli |
| 7-8 | Liquid | Assay Buffer | | |

Stability studies. The Chemibead reagent of the commercial kit was prepared in each of the three LOCI diluents mentioned above, namely, Control, Diluent 1 and Diluent 2. Five different concentrations of cTnI analyte in each diluent was studied; L1=0.01 ng/ml, L2=0.59 ng/ml, L3=6.2 ng/ml, L4=19.8 ng/ml and L5=42.15 ng/ml, respectively. The Chemibeads of the commercial kit (Chemibead 1) are polystyrene beads with chelated europium (chelate=NHA) and thioxene as the chemiluminescent composition. The Chemibeads comprise an aminodextran layer and an outer dextran aldehyde layer to which the anti-TnI antibody is conjugated.

In addition to the above, a second chemibead reagent (Chemibead 2) was studied. Chemibead 2 beads were carboxylated latex beads (Seradyn Inc., Indianapolis Ind., cat. #100229100440) with chelated europium (chelate=NHA) and thioxene as the chemiluminescent composition incorporated in the latex beads in a manner such as that disclosed in U.S. Pat. No. 5,811,311, the relevant disclosure of which is incorporated herein by reference. Anti-cTnI antibody was coupled to the surface of the beads using standard EDAC/NHS (1-ethyl-3-(3-dimethylaminopropyl)carbodiimide hydrochloride/N-hydroxy succinimide chemistry. Chemibead 1 was prepared in each of the three LOCI diluents mentioned above, namely, Control, Diluent 1 and Diluent 2. Five different concentrations of cTnI analyte in each diluent were studied as discussed above for Chemibead 1.

The stability study was carried out at two different temperatures, namely, 4° C. and 25° C. Signal generation using the commercial cTnI assay was studied at day 0, day 1, day 5, day 8 and day 28. The assays were conducted according to the manufacturer's instructions with the exception that Chemibead 1 and Chemibead 2 preparations were substituted for the commercial beads in commercial diluent. The results for Chemibead 1 are summarized in Table 2 and the results for Chemibead 2 are summarized in Table 3.

TABLE 2

| | | SIGNAL | | | | | |
|---|---|---|---|---|---|---|---|
| | | Control | Control | Chemibead 1 | Chemibead 1 | Chemibead 1 | Chemibead 1 |
| | | | | | [NHA] mg/L | | |
| | | 0 | 0 | 2 | 2 | 10 | 10 |
| | | | | TEMP ° C. | | | |
| DAY | | 4 | 25 | 4 | 25 | 4 | 25 |
| 0 | L1 | 7.4 | 7.4 | 7.8 | 7.8 | 8.1 | 8.1 |
| 0 | L2 | 31.9 | 31.9 | 33.3 | 33.3 | 33.6 | 33.6 |
| 0 | L3 | 341.6 | 341.6 | 358.8 | 358.8 | 359.6 | 359.6 |
| 0 | L4 | 1,402.5 | 1,402.5 | 1,464.8 | 1,464.8 | 1,464.2 | 1,464.2 |
| 0 | L5 | 3,285.3 | 3,285.3 | 3,413.0 | 3,413.0 | 3,383.2 | 3,383.2 |
| 1 | L1 | 7.2 | 6.9 | 7.7 | 8.0 | 8.0 | 7.7 |
| 1 | L2 | 32.6 | 31.5 | 33.8 | 33.5 | 33.1 | 33.2 |
| 1 | L3 | 361.0 | 343.3 | 359.1 | 353.7 | 364.5 | 359.0 |
| 1 | L4 | 1,470.8 | 1,436.1 | 1,492.9 | 1,463.2 | 1,533.8 | 1,475.3 |
| 1 | L5 | 3,441.9 | 3,379.4 | 3,510.9 | 3,431.7 | 3,520.9 | 3,463.7 |
| 5 | L1 | 7.5 | 6.7 | 7.8 | 7.0 | 7.8 | 7.1 |
| 5 | L2 | 32.6 | 29.4 | 33.4 | 30.0 | 33.4 | 30.1 |
| 5 | L3 | 351.3 | 312.0 | 356.1 | 319.5 | 362.3 | 323.1 |
| 5 | L4 | 1,454.3 | 1,297.5 | 1,490.2 | 1,319.6 | 1,485.6 | 1,345.0 |
| 5 | L5 | 3,394.6 | 3,017.7 | 3,504.7 | 3,109.9 | 3,469.0 | 3,151.0 |
| 8 | L1 | 7.4 | | 8.2 | | 7.7 | |
| 8 | L2 | 32.7 | | 34.0 | | 33.2 | |
| 8 | L3 | 353.8 | | 365.7 | | 362.9 | |
| 8 | L4 | 1,455.6 | | 1,493.4 | | 1,517.8 | |
| 8 | L5 | 3,441.9 | | 3,541.0 | | 3,551.2 | |
| 28 | L1 | 7.4 | 5.6 | 7.6 | 6.2 | 7.7 | 6.1 |
| 28 | L2 | 25.9 | 19.0 | 26.7 | 20.1 | 26.8 | 19.9 |
| 28 | L3 | 304.8 | 221.9 | 324.7 | 230.3 | 309.6 | 230.2 |
| 28 | L4 | 1,319.0 | 954.1 | 1,380.8 | 992.8 | 1,349.9 | 978.6 |
| 28 | L5 | 3,166.2 | 2,317.2 | 3,207.9 | 2,448.5 | 3,262.0 | 2,454.9 |

TABLE 3

| | | SIGNAL | | | | | |
|---|---|---|---|---|---|---|---|
| | | Control | Control | Chemibead 2 | Chemibead 2 | Chemibead 2 | Chemibead 2 |
| | | | | | [NHA] mg/L | | |
| | | 0 | 0 | 2 | 2 | 10 | 10 |
| | | | | TEMP ° C. | | | |
| DAY | | 4 | 25 | 4 | 25 | 4 | 25 |
| 0 | L1 | 7.5 | 7.5 | 8.3 | 8.3 | 8.4 | 8.4 |
| 0 | L2 | 30.0 | 30.0 | 33.9 | 33.9 | 34.2 | 34.2 |
| 0 | L3 | 352.1 | 352.1 | 394.4 | 394.4 | 390.5 | 390.5 |
| 0 | L4 | 1,414.3 | 1,414.3 | 1,570.0 | 1,570.0 | 1,549.6 | 1,549.6 |
| 0 | L5 | 3,281.4 | 3,281.4 | 3,619.8 | 3,619.8 | 3,598.7 | 3,598.7 |
| 1 | L1 | 7.4 | 6.8 | 8.4 | 7.9 | 8.8 | 8.3 |
| 1 | L2 | 30.6 | 27.1 | 34.2 | 31.7 | 35.4 | 33.2 |
| 1 | L3 | 360.8 | 306.9 | 390.7 | 358.2 | 407.0 | 380.0 |
| 1 | L4 | 1,461.9 | 1,260.8 | 1,584.8 | 1,467.2 | 1,630.1 | 1,548.2 |
| 1 | L5 | 3,382.0 | 2,962.7 | 3,660.5 | 3,366.2 | 3,761.9 | 3,630.5 |
| 5 | L1 | 7.1 | 5.7 | 8.1 | 6.7 | 8.6 | 7.4 |
| 5 | L2 | 29.9 | 19.7 | 32.7 | 24.9 | 34.0 | 27.0 |
| 5 | L3 | 335.0 | 210.9 | 372.4 | 265.3 | 382.9 | 317.2 |
| 5 | L4 | 1,378.5 | 873.5 | 1,517.1 | 1,080.1 | 1,563.2 | 1,260.8 |
| 5 | L5 | 3,242.3 | 2,118.8 | 3,547.0 | 2,700.2 | 3,439.1 | 2,925.4 |
| 8 | L1 | 7.4 | | 8.5 | | 9.1 | |
| 8 | L2 | 28.8 | | 34.0 | | 34.9 | |
| 8 | L3 | 335.5 | | 385.9 | | 394.4 | |
| 8 | L4 | 1,377.8 | | 1,548.9 | | 1,606.8 | |
| 8 | L5 | 3,174.2 | | 3,629.2 | | 3,765.2 | |
| 28 | L1 | 6.4 | 3.2 | 7.9 | 4.4 | 9.2 | 4.8 |
| 28 | L2 | 21.8 | 7.6 | 28.2 | 12.1 | 30.1 | 12.8 |
| 28 | L3 | 254.5 | 76.1 | 328.0 | 131.4 | 326.9 | 137.9 |
| 28 | L4 | 1,083.2 | 321.0 | 1,338.1 | 570.6 | 1,357.6 | 580.1 |
| 28 | L5 | 2,601.4 | 821.0 | 3,156.8 | 1,462.5 | 3,253.6 | 1,461.4 |

The above results demonstrate that NHA included in the diluent for the chemibead reagent provided significant stability during storage of the chemibead reagent solutions for up to 28 days at 4° C. and 25° C. as evidenced by enhanced signal generation over the Control.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. Furthermore, the foregoing description, for purposes of explanation, used specific nomenclature to provide a thorough understanding of the invention. However, it will be apparent to one skilled in the art that the specific details are not required in order to practice the invention. Thus, the foregoing descriptions of specific embodiments of the present invention are presented for purposes of illustration and description; they are not intended to be exhaustive or to limit the invention to the precise forms disclosed. Many modifications and variations are possible in view of the above teachings. The embodiments were chosen and described in order to explain the principles of the invention and its practical applications and to thereby enable others skilled in the art to utilize the invention.

What is claimed is:

1. A method of enhancing the stability of signal output by a chemiluminescent reagent comprising a solid support having associated therewith a chemiluminescent composition comprising a complex of a metal and one or more chelating agents, the method comprising incorporating into a medium comprising the chemiluminescent reagent one or more stabilizing agents selected from the group consisting of metal chelating agents and metal chelates in an amount sufficient to enhance the stability of signal output by the chemiluminescent reagent wherein the metal chelating agents that are stabilizing agents are selected from the group consisting of 2-(1',1',1',2',2',3',3'-heptafluoro-4',6'-hexanedion-6'-yl)-naphthylene, 4,4'-bis(2",3",3"-heptafluororo-4",6"-hexanedion-6"-yl)-o-terphenyl, phenanthroline, phenanthroline carboxylic acid, 4,7-diphenyl-1,10-phenanthroline (DPP), 3-(2-thienoyl, 1,1,1-trifluoroacetone (TTA), 3-(2-naphthoyl)-1,1,1-trifluoroacetone (NPPTA), (trioctyl phosphine oxide (TOPO), triphenyl phosphine oxide (TPPO), 3-benzoyl-1,1,1-trifluoroacetone (BFTA), 2,2-dimethyl-4-perfluorobutyoyl-3-butanone (fod), 2,2'-dipyridyl (bpy), salicylic acid, and bipyridylcarboxylic acid and wherein the metal chelates that are stabilizing agents are metal chelates of 2-(1',1',1',2',2',3',3'-heptafluoro-4',6'-hexanedion-6'-yl)-naphthylene, 4,4'-bis(2",3",3"-heptafluororo-4",6"-hexanedion-6"-yl)-o-terphenyl, phenanthroline, phenanthroline carboxylic acid, 4,7-diphenyl-1,10-phenanthroline (DPP), 3-(2-thienoyl, 1,1,1-trifluoroacetone (TTA), 3-(2-naphthoyl)-1,1,1-trifluoroacetone (NPPTA), (trioctyl phosphine oxide (TOPO), triphenyl phosphine oxide (TPPO), 3-benzoyl-1,1,1-trifluoroacetone (BFTA), 2,2-dimethyl-4-perfluorobutyoyl-3-butanone (fod), 2,2'-dipyridyl (bpy), salicylic acid, and bipyridylcarboxylic acid.

2. The method according to claim 1 wherein the stabilizing agent is a metal chelating agent of the complex.

3. The method according to claim 1 wherein the metal is a rare earth metal or a metal of Group VIII.

4. The method according to claim 1 wherein the metal is selected from the group consisting of europium, terbium, dysprosium, samarium osmium and ruthenium.

5. The method according to claim 1 wherein the metal is europium, the chelating agent is 2-(1',1',1',2',2',3',3'-heptafluoro-4',6'-hexanedion-6'-yl)-naphthylene and 4,7-diphenyl-1,10-phenanthroline and the stabilizing agent comprises 2-(1',1',1',2',2',3',3'-heptafluoro-4',6'-hexanedion-6'-yl)-naphthylene or 2-(1',1',1',2',2',3',3'-heptafluoro-4',6'-hexanedion-6'-yl)-naphthylene and 4,7-diphenyl-1,10-phenanthroline.

6. The method according to claim 1 wherein the solid support is a particle.

7. The method according to claim 1 wherein the solid support is a latex particle.

8. The method according to claim 1 wherein the complex is incorporated in the solid support.

9. The method according to claim 1 wherein a member of a specific binding pair is associated with the solid support.

10. A chemiluminescent reagent for determining the presence and/or amount of an analyte in a sample suspected of containing the analyte, the reagent comprising in a medium a solid support having associated therewith a member of a specific binding pair and having incorporated therein a complex of a metal and one or more chelating agents, wherein the medium further comprises one or more stabilizing agents selected from the group consisting of metal chelating agents and metal chelates, the amount of the one or more stabilizing agents being sufficient to enhance the stability of signal output by the chemiluminescent reagent wherein the metal chelating agents that are stabilizing agents are selected from the group consisting of 2-(1',1',1',2',2',3',3'-heptafluoro-4',6'-hexanedion-6'-yl)-naphthylene, 4,4'-bis(2",3",3"-heptafluororo-4",6"-hexanedion-6"-yl)-o-terphenyl, phenanthroline, phenanthroline carboxylic acid, 4,7-diphenyl-1,10-phenanthroline (DPP), 3-(2-thienoyl, 1,1,1-trifluoroacetone (TTA), 3-(2-naphthoyl)-1,1,1-trifluoroacetone (NPPTA), (trioctyl phosphine oxide (TOPO), triphenyl phosphine oxide (TPPO). 3-benzoyl-1,1,1-trifluoroacetone (BFTA), 2,2-dimethyl-4-perfluorobutyoyl-3-butanone (fod), 2,2'-dipyridyl (bpy), salicylic acid, and bipyridylcarboxylic acid and wherein the metal chelates that are stabilizing agents are metal chelates of 2-(1',1',1',2',2',3',3'-heptafluoro-4',6'-hexanedion-6'-yl)-naphthylene, 4,4'-bis(2",3",3"-heptafluororo-4",6"-hexanedion-6"-yl)-o-terphenyl, phenanthroline, phenanthroline carboxylic acid, 4,7-diphenyl-1,10-phenanthroline (DPP), 3-(2-thienoyl, 1,1,1-trifluoro acetone (TTA), 3-(2-naphtho yl)-1,1,1-trifluoro acetone (NPPTA), (trioctyl phosphine oxide (TOPO), triphenyl phosphine oxide (TPPO). 3-benzoyl-1,1,1-trifluoroacetone (BFTA), 2,2-dimethyl-4-perfluorobutyoyl-3-butanone (fod), 2,2'-dipyridyl (bpy), salicylic acid, and bipyridylcarboxylic acid.

11. The reagent according to claim 10 wherein the stabilizing agent is a chelating agent of the complex.

12. The reagent according to claim 10 wherein the metal is a rare earth metal or a metal of Group VIII.

13. The reagent according to claim 10 wherein the metal is selected from the group consisting of europium, terbium, dysprosium, samarium osmium and ruthenium.

14. The reagent according to claim 10 wherein the solid support is a particle.

15. The reagent according to claim 10 wherein the solid support is a latex particle.

16. The reagent according to claim 10 wherein the stabilizing agent is the same as the complex that is incorporated in the solid support.

17. The reagent according to claim 10 wherein the solid support further comprises a photosensitizer associated therewith.

18. The reagent according to claim 10 wherein the metal is europium, the chelating agent is 2-(1',1',1',2',2',3',3'-heptafluoro-4',6'-hexanedion-6'-yl)-naphthylene and 4,7-diphenyl-1,10-phenanthroline and the stabilizing agent comprises 2-(1',1',1',2',2',3',3'-heptafluoro-4',6'-hexanedion-6'-yl)-naphthylene or 2-(1',1',1',2',2',3',3'-heptafluoro-4',6'-hexanedion-6'-yl)-naphthylene and 4,7-diphenyl-1,10-phenanthroline.

19. A method for determining the presence and/or amount of an analyte in a sample suspected of containing the analyte, the method comprising:
 (a) providing in combination in a medium:
  (i) the sample,
  (ii) the chemiluminescent reagent of claim 10, and
  (iii) a photosensitizer associated with a particle and being capable of generating singlet oxygen, wherein a specific binding pair member for the analyte is associated with at least one of the solid support or the particle,
 (b) subjecting the combination to conditions for binding of the analyte to the specific binding pair member for the analyte, and
 (c) irradiating the photosensitizer with light and detecting the amount of luminescence generated by the chemiluminescent reagent, the amount of luminescence being related to the amount of the analyte in the sample.

20. The method according to claim 19 wherein the particle with which the photosensitizer is associated is the solid support of the chemiluminescent reagent.

21. The method according to claim 19 wherein the metal is europium, the chelating agent is 2-(1',1',1',2',2',3',3'-heptafluoro-4',6'-hexanedion-6'-yl)-naphthylene and 4,7-diphenyl-1,10-phenanthroline and the stabilizing agent comprises 2-(1',1',1',2',2',3',3'-heptafluoro-4',6'-hexanedion-6'-yl)-naphthylene or 2-(1',1',1',2',2',3',3'-heptafluoro-4',6'-hexanedion-6'-yl)-naphthylene and 4,7-diphenyl-1,10-phenanthroline.

\* \* \* \* \*